United States Patent de la Rama et al.

[11] Patent Number: 6,001,095
[45] Date of Patent: Dec. 14, 1999

[54] CATHETER SYSTEM HAVING CLOSELY SPACED DISTAL BIPOLAR ELECTRODES

[75] Inventors: Alan de la Rama, Cerritos; Weng-Kwen Raymond Chia, Irvine; Hosheng Tu, Tustin, all of Calif.

[73] Assignee: Irvine Biomedical, Inc., Irvine, Calif.

[21] Appl. No.: 09/066,274

[22] Filed: Apr. 24, 1998

Related U.S. Application Data

[62] Division of application No. 08/880,837, Jun. 23, 1997, Pat. No. 5,782,900.

[51] Int. Cl.$^6$ .......................... A61N 1/05; A61B 5/0402; A61B 17/39
[52] U.S. Cl. .......................... 606/41; 600/374; 607/101; 607/122
[58] Field of Search .................................. 600/373, 374, 600/377, 381; 607/119, 120, 122, 96, 99, 101, 102, 104, 105, 113, 116; 606/41, 46, 49

[56] References Cited

U.S. PATENT DOCUMENTS

| | | | |
|---|---|---|---|
| 4,592,372 | 6/1986 | Beramek | 607/119 |
| 4,832,048 | 5/1989 | Cohen | 606/41 |
| 4,960,134 | 10/1990 | Webster, Jr. | 607/116 |
| 5,324,324 | 6/1994 | Vachon et al. | 607/120 |
| 5,697,927 | 12/1997 | Imran et al. | 606/41 |
| 5,782,900 | 7/1998 | De La Rama et al. | 607/122 |

*Primary Examiner*—Jeffrey R. Jastrzab

[57] ABSTRACT

A catheter system suitable for electrophysiology mapping and radiofrequency ablation of cardiac tissue comprises a catheter shaft having a distal end, a proximal handle, and at least a lumen extending therebetween, wherein a distal section of the shaft is either a fixed curve type or a deflectable type; and safety means being provided to maintain the integrity of the catheter by holding the long tip electrode in place, wherein the safety means is a long tip electrode with an extended flexible stem having at least one open groove or slot on the stem.

4 Claims, 4 Drawing Sheets

CATHETER SYSTEM HAVING CLOSELY SPACED DISTAL BIPOLAR ELECTRODES

CROSS-REFERENCE TO RELATED APPLICATIONS

This is a division of Ser. No. 08/880,837, filed Jun. 23, 1997, now U.S. Pat. No. 5,782,900.

FIELD OF THE INVENTION

The present invention generally relates to improved constructions for a catheter system. More particularly, this invention relates to the methods and apparatus for diagnosing and treating cardiac arrhythmias via a cardiovascular catheter system having safety means to maintain the integrity of a closely spaced distal bipolar catheter system.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic region" or "accessory atrioventricular pathway" close to the inner surface of the chambers of a heart. The heart includes a number of normal pathways for the propagation of electrical signals from the upper to the lower chamber of the heart, which are necessary for performing normal function. The presence of arrhythmogenic region or accessory pathways can bypass or short circuit the normal pathways, potentially resulting in very rapid heart contractions, referred to here as tachycardias.

Cardiac mapping is used to locate aberrant electrical pathways and currents emanating within the heart. The aberrant pathways cause the heart muscle contractions to take on abnormal and life threatening dysrhythmias. Intracardiac mapping requires careful positioning of a plurality of catheters of multiple electrodes within the heart. For example, Webster, Jr. in U.S. Pat. No. 4,960,134 shows the general use of a catheter. It is important for a catheter to move into and out of the heart chamber freely without any obstruction or potential complications of components disengagement from the catheter shaft.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a clinician to be able to accurately steer the catheter to the region for ablation. Once at the region, it is important for a catheter to intimately contact the tissue site to effectively control the emission of energy to ablate the tissue within the heart.

Regardless of the type of mapping means or ablation means used, the clinician is called upon to remotely move, rotate, push, pull, and manipulate the catheters in various ways. First, a catheter is inserted into a major vein or artery, usually in the neck or groin area. It is then guided into the chambers of the heart by appropriate manipulation through the vein or artery. The distal section of a catheter must be maneuverable by a user from the proximal end of the catheter, so that the electrodes at the distal section can be positioned against the tissue at the desired location to assure that all aberrant electrical pathways are mapped and later ablated.

Development of prior catheters has focused upon the requirements of electrical continuity and interference problems. However, the mechanical and safety considerations have been overlooked. A conducting wire is soldered to the long tip electrode or the band electrode. The electrode with a conducting wire is thereafter placed and secured onto the catheter shaft, mostly by adhesives. The adhering force between a long tip electrode and the catheter shaft is proportional to the contact surface area. It has been reported that the long tip electrode might sometimes disengage from the distal section of the catheter shaft.

The frequency of the tip electrode disengagement becomes more often when a longer electrode is used for atrial flutter applications. In an atrial flutter procedure, a long tip electrode of 8 mm length or longer is generally required. In this case, the contact area for gluing between the stem of the electrode and the inner surface of the catheter shaft is not proportionally increased. The electrode is generally prone to separating from its main catheter shaft body because of inadequate contact area and subsequently gluing strength. The long tip electrode might inadvertently be separated from the catheter shaft and left behind in a patient's heart or in a circulation system. The prior development has overlooked the important need to provide a safe, intact catheter system having safety means in addition to the gluing force. It is the objective of this invention to provide the needed safety means for the electrophysiology cardiovascular catheter system having a long tip electrode.

SUMMARY OF THE INVENTION

It is an object of the present invention to provide an improved catheter system which can be used in mapping and ablating the arrhythmogenic region. It is another object of the present invention to provide a safety means to the catheter system so that the integrity of the catheter is maintained throughout clinical procedures.

In one embodiment, a catheter system of this invention comprises a catheter shaft having a distal section, a distal end, a proximal end, and at least one lumen extending therebetween; a handle attached to the proximal end of the shaft; a plurality of electrodes disposed at the distal section, wherein a long tip electrode is secured at the distal end of the catheter; and an extended stem of the long tip electrode having a proximal end, a distal end, and at least one open groove or slot in the axial direction on the surface of the stem, wherein the open groove or slot is extended over the whole length of the stem. In an alternate embodiment, the extended stem of the long tip electrode is a flexible stem The open groove or slot on the stem is to provide adequate clearance for at least one conducting wire to enter from the adjacent band electrode into the lumen. The extended flexible stem may be composed of the material such as the braided metal mesh in a spiral-convoluted form. In one embodiment, the length of the extended stem is equal to or longer than the length of the exterior surface of the long tip electrode. In a preferred embodiment, the proximal end of the stem having at least one open groove or slot extends proximally beyond the distal edge of a first band electrode. The purpose is to make a catheter system having closely separated bipolar electrodes at the catheter tip.

The distal section of the catheter system of this invention can be either a fixed curve type or a deflectable curve type. In an exemplary embodiment, the means for deflecting the distal section of the steerable catheter comprises at least two pull wires along with a support wire. The pull wires are attached to radially offset locations at the distal end of the deflectable section of the catheter shaft whereas at least a support wire radially in-between the pull wires, and means at the proximal end of the shaft for selectively applying tension to the pull wires to cause deflection of the deflectable portion. In certain cases, the function of a support wire can be substituted by a spring coil which is stationary at its proximal end with respect to the shaft. The catheter system further comprises a steering mechanism at the handle, wherein the steering mechanism provides a plurality of deflectable curves on the tip section of the catheter assembly. The incorporation of the steering mechanism in a catheter is well known to those who are skilled in the art.

Usually, in another embodiment for a steerable catheter of this invention, the distal section of the shaft may include at least three radially offset lumens, and wherein the two pull wires and one support wire are disposed in the central lumen of the catheter shaft over a proximal section thereof; the two pull wires are disposed in the radially offset lumens over the distal section thereof, and the support wire is disposed in the central lumen.

The means for selectively applying tension comprises a steering mechanism in the handle, and the means for applying torque to the core wire comprises a rotatable ring or push-pull button disposed on the handle, the ring or button being coupled to the proximal end of the core wire. A variety of other tension applying mechanisms, such as joy sticks, may also be employed.

Signal conducting electrodes are placed on the distal section while their insulated conducting wires are passed through the shaft lumen to the connector secured at the proximal end of the handle. The main purpose of the conducting wires is to transmit the electric signal and to provide means for RF energy delivery. The extended flexible stem on the long tip electrode reinforces the adhesive strength of the long tip electrode.

A method for positioning a catheter system, having a safety means at its distal section within a heart chamber, comprises percutaneously introducing the distal end of a catheter through an artery or vein to the heart chamber. Once the catheter long tip is at the desired location, the handle at the proximal end is connected to the EKG monitor. And the electrical signal from the electrodes on the distal section can be transmitted to the exterior EKG monitor for cardiac mapping. Alternately, the radio frequency energy can be supplied to one or more of the electrodes on the distal section once an intimate contact with the tissue is achieved, using the catheter of this invention.

The method and apparatus of the present invention have several significant safety advantages over known catheters. In particular, the extended flexible stem with an open groove or slot on the long tip electrode maintains the integrity of the catheter system from potential complications of undesired component disengagement.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
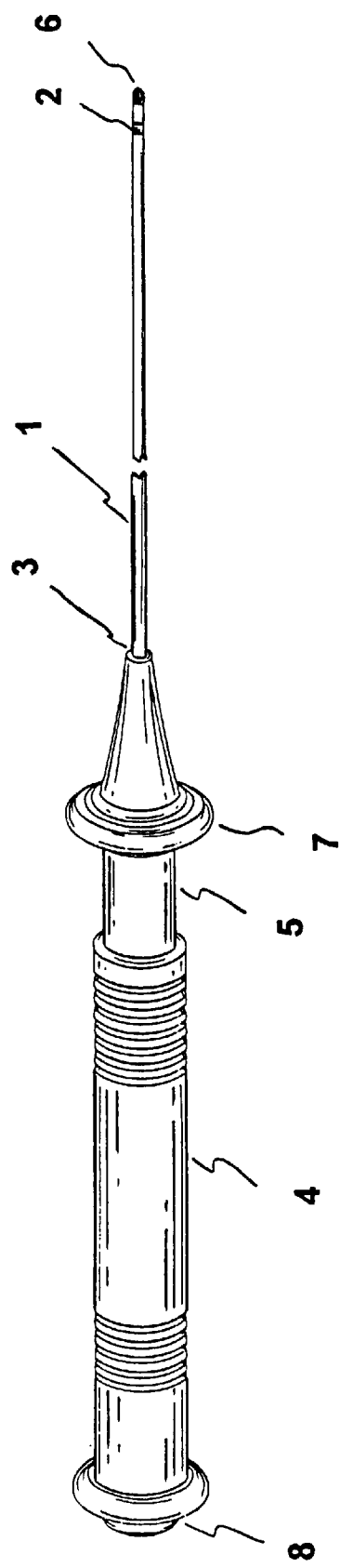
FIG. 1 is an overall view of the catheter system, including safety means, constructed in accordance with the principles of the present invention.

FIG. 1 shows a catheter system constructed in accordance with the principles of the present invention comprising: a catheter shaft 1 having a distal tip section 2, a distal end 6, a proximal end 3 and at least one lumen extending therebetween. A handle 4 is attached to the proximal end 3 of the catheter shaft 1. The tip section 2 may be a fixed curve type or a deflectable type by employing a steering mechanism 5 at the handle 4. A push-pull plunger 7 is employed to deflect the tip section 2 of the catheter shaft 1. A connector 8 is secured at the proximal end of the handle 4. At least one electrode available for electrophysiology use, is disposed on the tip section 2.

Figure 2:
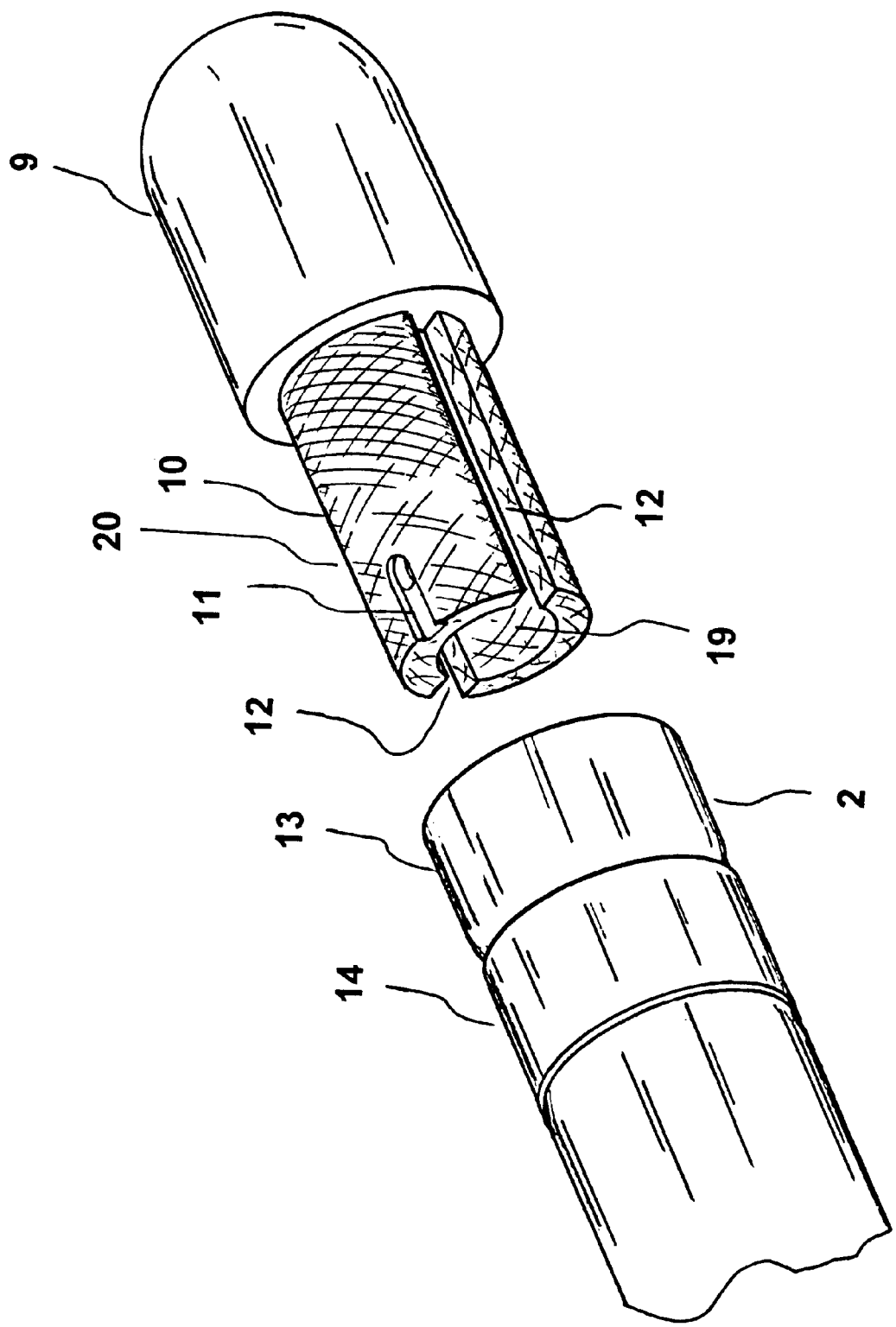
FIG. 2 is a perspective view of the distal section of the catheter system with an extended flexible stem as a safety means.

FIG. 2 shows a perspective view of the distal section of a catheter system with an extended flexible stem as a safety means. The long tip electrode 9 which has a long stem 10 and has at least one open groove 11 or slot 12 on the stem 10 is to be fitted into the catheter shaft 13 of the catheter system. In one embodiment, the stem 10 has a hollow center 19. At least one band electrode 14 is secured at the distal tip section 2 of the catheter system. A conducting wire 17 from the band electrode 14 passes through the catheter shaft 13 through a small opening 18 on the catheter shaft and enters into the lumen 15 and is thereafter secured to the connector 8 at the proximal end of the handle 4. When inserting the long tip electrode 9 into the catheter shaft 13, The open groove 11 or slot 12 of the stem 10 by-passes the conducting wire 17 entering from the band electrode 14. Therefore, a band electrode 14 can be located very close to the long tip electrode 9 to form a distal bipolar electrode system without concern for the obstruction of the long stem extending from the long tip electrode. The length of the stem can therefore be as long as one wishes and the open groove or slot can be any length. The stem may be composed of the material such as the braided metal mesh 20 in a spiral-convoluted form.

Figure 3:
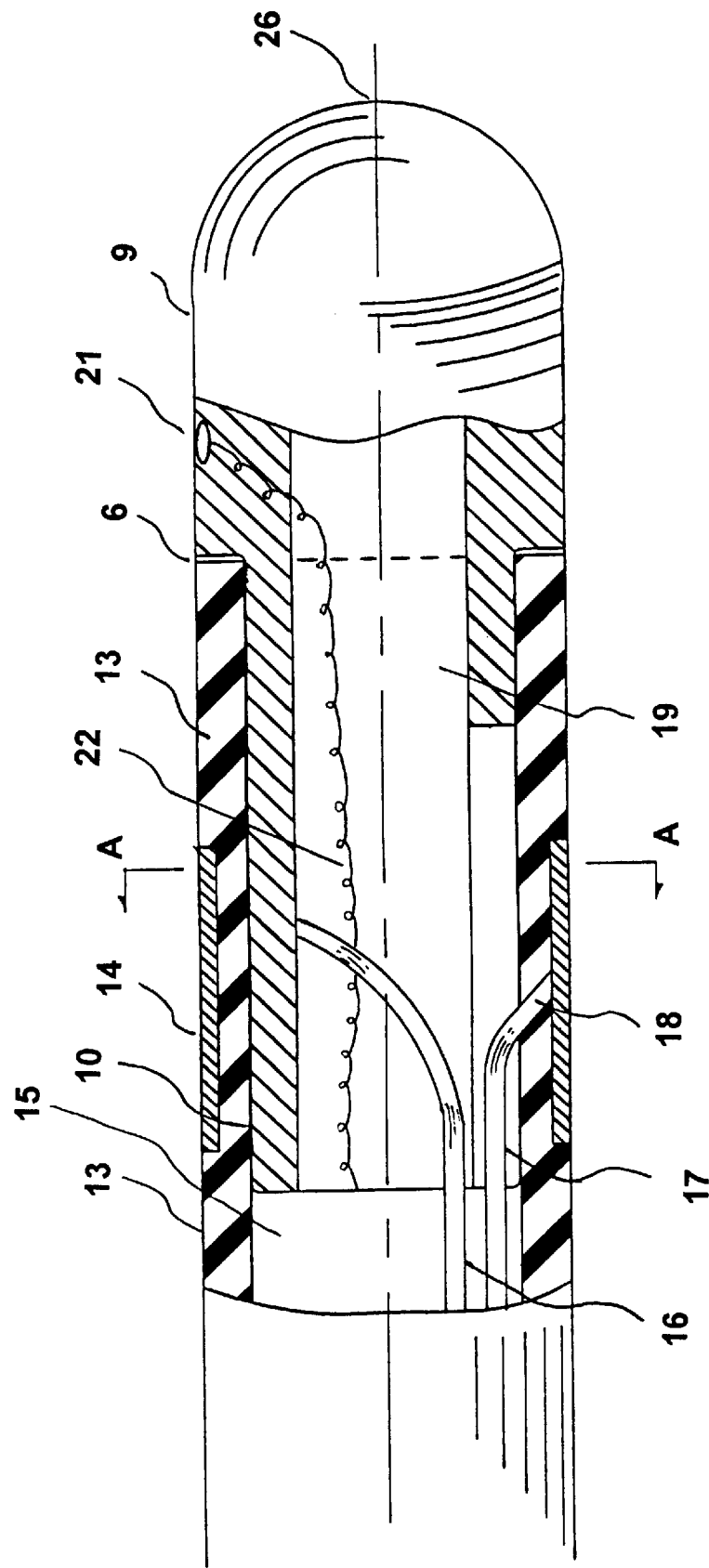
FIG. 3 is a close-up view of the distal section of the catheter system of FIG. 2.

FIG. 3 shows a close-up view of the distal section of the catheter system of FIG. 2. During a catheter fabrication process, a long tip electrode 9 with a long stem 10 is attached to the catheter shaft 13 using either epoxy or glue type adhesive. A conducting wire 16 for the long tip electrode 9 is used for EKG signal monitoring and for RF energy transmission. At least one other conducting wire 17 for the band electrode 14 is used for EKG signal monitoring. The distal tip 26 of the long electrode 9 is generally smooth for contacting the tissue.

Figure 4:
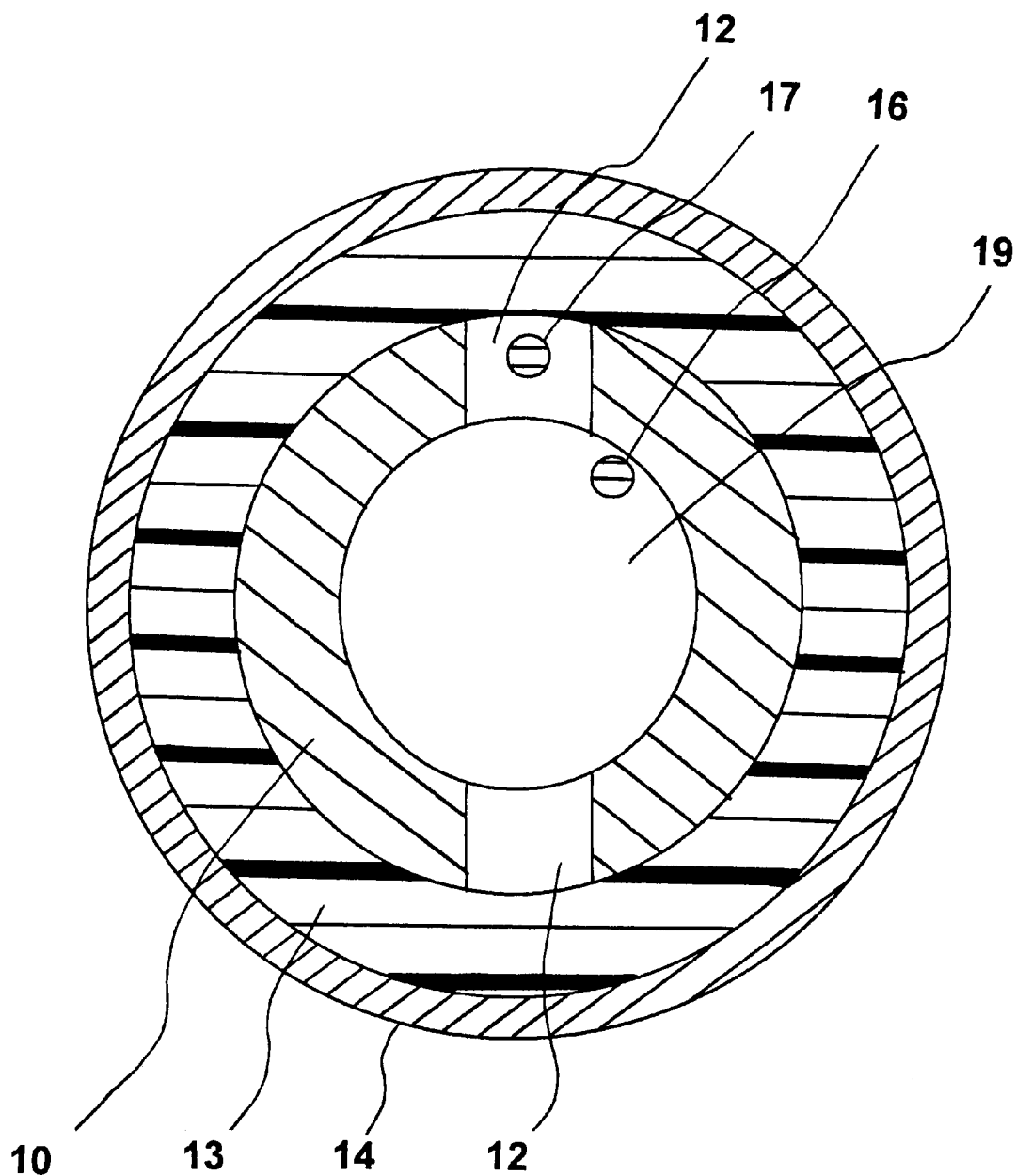
FIG. 4 is a cross-sectional view, section A—A, of the distal section of the catheter system of FIG. 3.

FIG. 4 shows a cross-sectional view, section A—A, of the distal section of the catheter system of FIG. 3. The band electrode 14 overlays the top of the catheter shaft 13. The stem 10 of the long tip electrode 9 lies tightly underneath the catheter shaft 13. The conducting wire 17 from the band electrode 14 stays without any obstruction in the space provided by the open groove 11 or slot 12 of the stem 10. In one embodiment, another open groove 11 or slot 12 is provided at an appropriate orientation of the stem 10. The stem can be made of a flexible material. This flexible stem, which has a hollow center 19, is especially useful in the distal tip section of a deflectable catheter. In an alternate embodiment, a temperature sensor 21 with transmission means 22 is secured about the surface of the tip electrode 9.

In another embodiment, the steerable catheter of the present invention comprises a handle and a catheter shaft, wherein a long tip electrode and at least one band electrode are disposed at the distal section of the catheter shaft. The steerable catheter has a push-pull plunger as a steering mechanism to deflect the long tip of the catheter to a desired curve type.

The material of electrodes may be selected from the group of platinum, iridium, silver, gold or stainless steel. The spacing between the electrodes is in the range of 1 mm to 10 mm, preferably 2 to 5 mm. The length of the stem is in the range of 2 mm to 20 mm, preferably 2 to 10 mm.

From the foregoing, it should now be appreciated that an improved catheter system has been disclosed, herein comprised of safety means to render a catheter less prone to disengagement. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

(a) a catheter shaft having a distal section, a distal end, a proximal end, and at least one lumen extending therebetween;

(b) a handle attached to the proximal end of the catheter shaft;

(c) a plurality of electrodes disposed at the distal section, each of the plurality of electrodes having an electrical conductor, wherein a long tip electrode is secured at the distal end of the catheter; and (d) a flexible extended stem of the long tip electrode having a proximal end, a distal end, and at least one open slot in the axial direction on the surface of said stem, wherein the open slot is extended over a portion of the length of said stem.

2. The catheter system of claim 1, wherein the flexible extended stem is a braided metal mesh in a spiral-convoluted form.

3. The catheter system of claim 1, wherein the length of the flexible extended stem is longer than the length of an outer surface of the long tip electrode.

4. The catheter system as in claim 1 further comprising a first band electrode on the catheter shaft, having a proximal end and a distal end, wherein the proximal end of the flexible extended stem extends beyond the distal end of the first band electrode.

* * * * *